United States Patent [19]
Montner et al.

[11] Patent Number: 5,811,600
[45] Date of Patent: Sep. 22, 1998

[54] GLYCEROL ENHANCED REHYDRATION FORMULATION

[75] Inventors: Paul Montner; Dan Stark, both of Albuquerque, N. Mex.

[73] Assignee: University of New Mexico, Albuquerque, N. Mex.

[21] Appl. No.: 873,752

[22] Filed: Jun. 12, 1997

Related U.S. Application Data

[63] Continuation of Ser. No. 415,380, Apr. 3, 1995, abandoned, which is a continuation-in-part of Ser. No. 55,003, Apr. 30, 1993, Pat. No. 5,403,921.

[51] Int. Cl.⁶ .............................. C07C 31/18; C07H 1/00; C07G 17/00
[52] U.S. Cl. ...................... 568/852; 536/1.11; 536/123.1; 536/124
[58] Field of Search ............................ 568/852; 536/1.11, 536/123.1, 124

[56] References Cited

U.S. PATENT DOCUMENTS

| | | | |
|---|---|---|---|
| 4,574,085 | 3/1986 | Dolkart et al. | 568/852 |
| 5,147,650 | 9/1992 | Fregly et al. | 568/852 |
| 5,210,083 | 5/1993 | Pfirrmann | 568/852 |
| 5,403,921 | 4/1995 | Montrer et al. | 536/1.11 |

*Primary Examiner*—Louise N. Leary
*Attorney, Agent, or Firm*—Hoffman, Wasson & Gitler

[57] ABSTRACT

A rehydration formulation which enhances a subjects ability to quickly recover from dehydration. The rehydration formulation includes a glycerol solution combined with a carbohydrate or sodium to produce a desired result. The glycerol solution combats the ill-effects of dehydration by increasing plasma osmolality thereby preventing loss of osmotic stimulus to thirst and enabling full rehydration to occur.

17 Claims, No Drawings

GLYCEROL ENHANCED REHYDRATION FORMULATION

This is a continuation of application Ser. No. 08/415,380 filed on Apr. 3, 1995 now abandoned, which was a continuation-in-part of Ser. No. 08/055,003, filed Apr. 30, 1993, which issued into U.S. Pat. No. 5,403,921.

GOVERNMENT RIGHTS

This invention was made in the performance of work supported by the National Institute of Health GCRC Award #5MOIRR00997-16 through the University of New Mexico Clinical Research Center, and the U.S. Government has certain rights therein.

BACKGROUND OF THE INVENTION

The present invention relates to an exercise regimen which enhances exercise endurance by hydration with a glycerol solution prior to inception of exercise, combined with hydration during exercise with a glycerol and carbohydrate based solution to optimize endurance. In addition, the invention relates to a glycerol formulation ingested to combat the ill-effects of dehydration. Dehydration can result in adverse physiologic changes, clinical symptoms and impaired performance. These include increased heart rate, elevated temperature, lower cardiac output and reduced skin blood flow.

Oral replacement solutions are widely used in athletic and recreational events. Strenuous exercise, water immersion, extreme cold, as well as exposure to sunlight and heat can cause significant physiological changes. Subjects exercising or working in the heat or for prolonged periods of time are at risk for developing impaired function or heat-related injuries. In order to prevent heat-related injuries such as heat exhaustion, heat stroke and dehydration syndrome, a number of compositions and solutions have been suggested.

In the Runner's World article, entitled "*HYPERHYDRATION*" by Liz Applegate (September 1992), glycerol has been suggested as a way to preserve blood volume, moderate heart rate and allow more blood to be sent to the skin for cooling. No analysis of a particular use or regimen is discussed nor are there specifics given concerning when to use it or in what combination or proportions thereof.

Further, in a published study by Koenigsberg et al, entitled, "40 *hour Glycerol-Induced Hyperhydration*", there is some evidence that glycerol hyperhydration can be maintained for up to 40 hours with ongoing ingestion of glycerol.

In "*Hyperhydration with glycerol solutions*", authored by Riedesel et al, American Physiological Society, 1987, glycerol was studied and its affect on dilute saline solution retention as well as general fluid retention.

In "*Effects of glycerol-induced hyperhydration prior to exercise in the heat on sweating and core temperature*", authored by Lyons et al, Medicine and Science in Sports and Exercise, 1990, the effects of glycerol induced hyperhydration prior to exercise in the heat or sweating and core temperature was studied. Here, exercise was started 2.5 hours after the fluids were ingested. The study concluded that glycerol induced hyperhydration reduced the thermal burden of moderate exercise.

In addition, U.S. Pat. No. 5,147,650, issued on Sep. 15, 1992, found that glycerol containing solution, compared to water or Gatorade® type drink, ingested during exercise resulted in an expanded blood volume, lower heart rate, and lower rectal temperature during exercise.

Further, dehydration of a subject is a significant concern. When dehydration is severe enough (about 3% of body weight) symptoms of lightheadedness, disorientation and fatigue ensure. Thus, performance and endurance are impaired.

Compared to several animal species, humans have an inadequate mechanism to replace fluid losses which occur during dehydration. This phenomena is known as involuntary dehydration.

When water alone is used for rehydration, plasma sodium and osmolality return to normal rapidly and osmotic contribution to thirst is lost.

In addition, the reduced plasma volume is restored early and the volume contribution to thirst is lost. Thus, drinking water to rehydrate reduces thirst and drive to replace losses. Furthermore, urine production is stimulated by these changes. In one study, after dehydration, followed by rehydration with water, subjects restored approximately 70% of lost fluid, and with a sodium solution, 80% was restored.

The invention herein described is a novel exercise regimen and composition for enhancing endurance and performance in activities such as hiking, soccer, football, etc., and allowing for one to combat the ill-effects of dehydration.

BRIEF SUMMARY OF THE INVENTION

The invention relates to a novel exercise regimen for ameliorating the adverse physiological effects which result from physical exertion and heat exposure. The subject hydration regimen comprises the steps of: ingesting a solution of glycerol and water prior to inception of the exercise. The subject begins ingestion of the solution, at a given rate by mouth, two hours before the inception of the exercise and stops ½ hour prior to inception. The subject begins to exercise and ingests a second solution comprising glycerol, carbohydrate, sodium and water at a given rate during exercise.

Combination of a pre-exercise glycerol solution hydration regimen with a glycerol/carbohydrate/sodium solution hydration regimen during exercise results in an unique and optimal methodology for improving endurance performance.

In addition, a glycerol containing solution offers an efficient method to combat the ill-effects of dehydration.

A glycerol containing solution offers several advantages for rehydration. A glycerol and water combination can increase plasma osmolality. Thus, the osmotic stimulus to thirst will not be lost. Additionally, a specified amount of glycerol and water can reduce urine output and cause fluid retention compared to water alone.

DETAILED DESCRIPTION OF THE INVENTION

The invention described herein is a novel exercise hydration regimen and rehydration formulation which has been shown to improve physiological response in subjects. Specifically, the pre-exercise portion of the invention comprises an exercise hydration regimen wherein a solution of from 0.78–2.0 gms/kg of glycerol and 26 ml/kg of water are ingested by mouth starting 2 hours before and continuing up until ½ hour before the start of exercise. This would correspond to a 3–8% solution of glycerol, and preferably a 4.6% solution. Total volume ingested over the 1½ hour hydration period is 26 ml/kg. This pre-exercise hydration regimen is then supplemented by fluid replacement during exercise. A second solution is ingested during exercise to prolong the benefit of the pre-exercise hydration. The second solution comprises from 0.4 to 1.5% glycerol, from 6–8% of a carbohydrate such as glucose and from 0–10 meq sodium, ingested at a rate of 800–1600 ml/hr.

Glycerol hyperhydration can be maintained for up to forty hours with ongoing ingestion of glycerol. A glycerol containing solution, compared to water or glucose, results in expended blood volume, lower heart rate, and lower rectal temperature. These beneficial physiological effects improve performance.

However, gastric emptying rates are impaired by high osmolality. For example, ½ of a 5% solution of carbohydrate (250 mosm) would be emptied in 20 minutes while ½ of 12.5% solution (675 mosm) would be emptied in 45 minutes. Thus solutions containing greater than 1.5% glycerol in addition to 6% glucose significantly impair gastric emptying. A solution containing from 0.4 to 1.5% glycerol, in addition to 6–8% carbohydrate (glucose) and 0–10 Meq sodium, ingested at a rate of 800–1600 ml/hr enhance hydration during exercise and prolong performance.

A rehydration glycerol formulation embodying the invention contains between 2% and 8% glycerol. In addition, the solution can contain up to 30 meq sodium for greater efficacy. The sodium helps maintain plasma osmolality, maintain thirst and improve palatability. Further, the solution can include carbohydrates. Inclusion of up to 8% carbohydrates enhances fluid retention and replenishes glycogen stores after prolonged exercise.

The glycerol rehydration product can be produced in liquid concentrate form and mixed with water to form a glycerol solution embodying the invention. The concentrate, when hydrated, contains from 2% to 8% glycerol in the resulting solution. Further, carbohydrates can be added to the concentrate or resulting solution in an amount of up to 8% and likewise sodium can be added to the powder or resulting solution in an amount up to 30 Meq. The additives enhance the flavor and restore the glycogen stores depleted during exercise.

EXAMPLE

A solution containing 2.67% glycerol was tested to measure rehydration efficacy versus a pure water solution.

Subjects were tested for weight loss during a four hour period of dehydration. The subjects lost approximately 3.4% of their overall body weight. Rehydration with a glycerol solution (2.67%) resulted in restoration to 99.5% of original body weight within 3 hours.

In another study, subjects were treated with a pure water solution and obtained restoration level of approximately 70% of original body weight, while the addition of sodium to the water solution only raised the restoration level to approximately 80% of the original body weight.

The combination of pre-exercise glycerol enhanced hydration regimen and glycerol enhanced hydration regimen during exercise produces a unique and optimal exercise regimen to enhance endurance and performance. Further, the use of a glycerol solution to treat dehydration enables a subject to have a quick recovery and combat the ill-effects of the state.

What is claimed is:

1. A rehydration formulation consisting essentially of glycerol, water and sodium.

2. The rehydration formulation as claimed in claim 1 comprising about 2 to 8 percent (vol./weight) glycerol.

3. The rehydration formulation as claimed in claim 1 comprising up to 30 meq. of sodium.

4. The rehydration formulation as claimed in claim 1 comprising about 2.67 percent (vol./weight) glycerol.

5. The rehydration formulation as claimed in claim 1 comprising insufficient carbohydrate to reduce osmolality, insufficient carbohydrate to reduce thirst, and insufficient carbohydrate to increase urination.

6. A method of improving rehydration of an animal body after exercise induced dehydration which comprises ingesting an aqueous solution comprising about 2 to 8 percent (vol./weight) of glycerol and insufficient carbohydrate to reduce thirst, reduce osmolality, and increase urination.

7. The method as claimed in claim 6 wherein said aqueous solution further comprises sodium.

8. The method as claimed in claim 7 wherein said sodium is present in said solution in a proportion of up to about 30 meq.

9. The method as claimed in claim 6 wherein said animal is human.

10. A method of retaining hydration of an animal body after exercise during which an aqueous solution comprising glycerol was ingested in an amount insufficient to prevent substantial dehydration, which method comprises ingesting an aqueous solution comprising about 2 to 8 percent (vol./weight) of glycerol and insufficient carbohydrate to reduce thirst, reduce osmolality, and increase urination.

11. The method as claimed in claim 10 wherein said aqueous solution further comprises sodium.

12. The method as claimed in claim 11 wherein said sodium is present in said solution on a proportion of up to about 30 meq.

13. The method as claimed in claim 10 wherein said animal is human.

14. A method of retaining hydration of an animal body after exercise wherein, prior to said exercise said body ingested an aqueous solution comprising about 2 to 8 percent (vol./weight) glycerol, which method comprises ingesting, after concluding said exercise, a post exercise, aqueous solution comprising about 2 to 8 percent (vol./weight) of glycerol and insufficient carbohydrate to reduce thirst, reduce osmolality, and increase urination.

15. The method as claimed in claim 14 wherein said post exercise, aqueous solution further comprises sodium.

16. The method as claimed in claim 15 wherein said sodium is present in said post exercise, aqueous solution in a proportion of up to about 30 meq.

17. The method as claimed in claim 14 wherein said body is human.

\* \* \* \* \*